United States Patent [19]

Ishii et al.

[11] 4,346,610
[45] Aug. 31, 1982

[54] DEVICE FOR INTRODUCING MICRO AMOUNT OF SAMPLE INTO AN ANALYZING APPARATUS

[75] Inventors: Daido Ishii, Nagoya; Hideki Konishi, Tokyo, both of Japan

[73] Assignee: Japan Spectroscopic Co., Ltd., Tokyo, Japan

[21] Appl. No.: 139,698

[22] Filed: Apr. 11, 1980

[30] Foreign Application Priority Data

Apr. 28, 1979 [JP] Japan .................................. 54-53126

[51] Int. Cl.³ .............................................. G01N 1/20
[52] U.S. Cl. .................................................. 73/863.73
[58] Field of Search ........ 73/422 GC, 863.73, 863.72, 73/863.71; 137/625.15, 625.46

[56] References Cited

U.S. PATENT DOCUMENTS

| | | | |
|---|---|---|---|
| 2,757,541 | 8/1956 | Watson | 73/422 GC |
| 2,973,117 | 2/1961 | Conklin | 73/863.73 |
| 3,080,759 | 3/1963 | McQuaid | 73/422 GC |
| 3,504,799 | 4/1970 | Ogle | 73/422 GC |
| 3,747,630 | 7/1973 | Hurrell | 137/625.46 |
| 3,885,439 | 5/1975 | Stone | 73/863.73 |
| 4,112,766 | 9/1978 | Ragains | 73/422 GC |

*Primary Examiner*—S. Clement Swisher
*Attorney, Agent, or Firm*—Browdy and Neimark

[57] ABSTRACT

A sample introducing device, placed in the midway of an analyzing apparatus having a sample flowing route and a carrier fluid flowing route, in which device a valve disc rotatably disposed under urging force between a pair of supporting members, provided with a sample flowing passage and a carrier fluid flowing passage, in a sandwiched manner, is manually rotated with a handle so as to switch a sample flowing hole made in the valve disc for containing a predetermined amount of a sample to a position alignable with the carrier fluid flowing passage. By this simple operation of rotating the valve disc the desired amount of the sample can be transferred to the carrier fluid flowing passage, through the switching over of the sample flowing hole, for being flowed to an apparatus for analysis.

11 Claims, 6 Drawing Figures

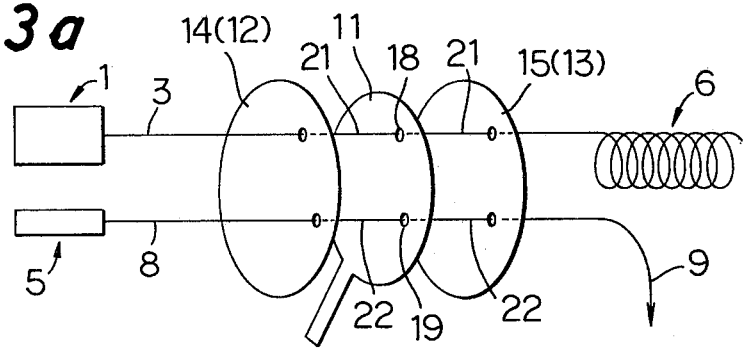
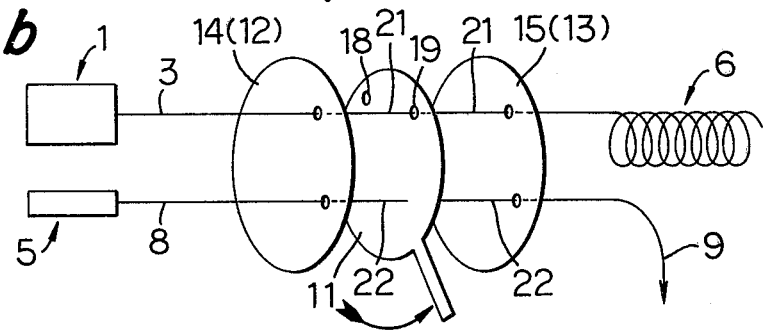
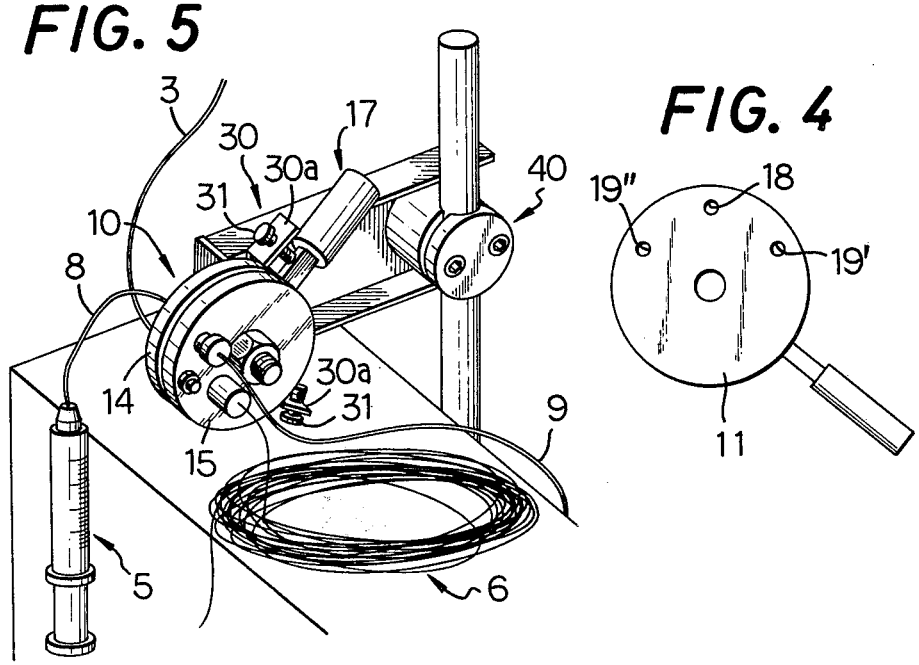

DEVICE FOR INTRODUCING MICRO AMOUNT OF SAMPLE INTO AN ANALYZING APPARATUS

FIELD OF THE INVENTION

This invention relates to a device for introducing micro amount of sample to an analysing apparatus such as a chromatographic apparatus, and more particularly to a micro amount sample introducing device preferably applied to a liquid chromatograph (hereinafter simply called LC), and specifically to a micro-high-performance LC.

BACKGROUND OF THE INVENTION

In recent years microanalysis technology in the field of liquid chromatography has been remarkably improved. Particularly super microanalysis technology, wherein a sample less than 1 $\mu$l and further minute amount ranging 0.01–0.3 $\mu$l is taken up as an object of analysis, has been developed as micro-high-performance LC. It has become one of the most important problems in the development of the latest LC how to pick up minute amount of a sample, precisely and in a good reproductive state, for introducing the same into a chromatographic column. In a gas chromatography (hereinafter simply called GC), which is also a representative one in parallel with the liquid chromatography in the field of chromatographic separating technology, it is a highly desirable thing to reduce the amount of the sample introduced, since the amount of the sample actually used in the separation process in the column is very small. Development of the micro amount sample introducing device is also greatly desired in this field of GC so as to make the microanalysis in GC possible.

In the conventional sample introducing devices, such as a micro-syringe which has been widely employed in LC, the disadvantages are inevitable.

(1) Since the micro-syringe determines the sample amount by the graduation impressed thereon, it is quite difficult to exactly pick up micro amount of the sample less than 1 $\mu$l and to introduce it into the chromatographic system. Personal variation in the handling amount is also inevitable in this case.

(2) Thickness of a syringe needle in the micro-syringe is non-negligibly great compared to the inside diameter of the column which is less than 1 mm, and further sometimes less than 0.1 mm; so the liquid is liable to be so disturbed, while the sample is introduced and the needle is removed, as to affect the chromatogram obtained from the development of the sample.

(3) When a micro column of small inside diameter is used for analysing micro amount of the sample, it is required to minimize the dead volume above and below the column to the greatest extent for preventing the diffusion of the sample. In the introduction of the sample by a conventional syringe, as injection port is needed to be disposed at the inlet of the column, so it is extremely difficult again to reduce the dead volume here.

As the conventional sample introducing devices, sample valves such as a four-port valve, a six-port injection valve are fairy widely utilized. They are indeed useful in the introduction, while holding good reproducibility, of a sample in the amount as small as to a few micro-liters. As they have such a structure as to pick up a sample into a sample loop therein, before rotating a rotating portion of the device for connecting the sample loop to the solvent line, so that the sample may be introduced into the column, there appears an annoying problem that minimizing the inside capacity of the sample loop is impossible. From the technical stand point of view sample picking up less than 2 $\mu$l, to say nothing of less than 1 $\mu$l, is impossible. So they are inappropriate as a micro sample introducing device or apparatus.

With the background mentioned above the inventors of this invention proposed a novel method of introducing a sample in a micro LC and an apparatus therefor, which are described in U.S. Pat. No. 4,102,782. It discloses that even a minute amount of sample less than 1 $\mu$l can be surely introduced into a column. The method and the apparatus are however still unsatisfactory in some respects such as: (1) Sample introduction operation and consequently chromatographic separation process still contains some complexity, because the sucking and delivering of the sample into the column is carried out by a pulse-motor which is forwardly and oppositely rotatable, and a mobile phase supplying line must be removed temporarily from the column so as to immerse the opening end thereof into a sample solution. And (2) the opening end of the mobile phase supplying line (a retainer tube) which has been immersed in the sample solution must be completely wiped off to remove the residue of sample stuck on the outer surface thereof. It makes the sample introduction operation considerably troublesome, and unless the wipe-off operation of the sample is enough the reproducibility of the sample will be affected.

SUMMARY OF THE INVENTION

This invention was made as a further improvement of the previous one after a series of studies and experiments by the inventors.

The primary object of this invention is to provide a micro amount sample introducing device, which is preferably applicable to an apparatus for analysis such as a chromatographic separating apparatus and more particularly to a micro-high-performance LC, capable of being completely mechanically operated, having eliminated all of the conventional disadvantages, for unconditionally or definitely introducing a sample into the column.

Another object of this invention is to provide a device of this kind allowing no personal variation in the handling operation thereof, and assuring good reproducibility, accurate amount picking up and easy introduction, of the sample.

Other objects of this invention will become apparent to those skilled in the art from the following detailed description of the preferred embodiments when read in conjunction with the accompanying drawings.

Such objects of this invention can be realized by a device which comprises a valve disc rotatable about the axis thereof which is perpendicular to the surface of the valve disc, a pair of supporting members disposed on either side of, and for urging the same from either side of, the valve disc, and has the under-mentioned structure and function: (1) the valve disc is provided with at least one carrier fluid flowing hole and at least one sample flowing hole having the same capacity as the desired sample amount to be introduced, both holes being formed piercing through, and on a same circumferential circle with the center at the rotational axis of, the valve disc; (2) each of the two supporting members is provided with at least one carrier fluid flowing passage and at least one sample flowing passage formed piercing through each member at a position to be registerable or alignable respectively with at least one of the carrier fluid flowing holes and at least one of the sample flowing holes; (3) the sample flowing hole communicated with the sample flowing passage can be moved owing to rotation of the valve disc to a position, with the sample held therein at an amount identical to the interior capacity thereof, communicatable with the carrier fluid flowing passage; and (4) the sample held in the sample flowing hole is flowed into an apparatus for analysis together with the carrier fluid in a sandwiched state by the carrier fluid flowing up-and downstream of the sample, for being analised.

As mentioned above, the sample flowed through the sample flowing passage is, at an amount identical to the capacity of the sample flowing hole, partially transferred into the carrier fluid flowing passage, by means of rotating the valve disc containing the sample flowing hole therein to a position wherein the sample flowing hole can be communicated with the carrier fluid flowing passage replacing the carrier fluid flowing hole, with the aid of the supporting members which urge the valve disc from either side like a sandwich so as to completely seal all of the flowing passages and the holes mentioned above. By such a transference of the sample in the predetermined amount to the carrier fluid flowing passage in a sandwiched manner by the carrier fluid in the up-and downstream, any of the variation of the sample amount according to the personal handling operation can be eliminated. It assures the good reproductivity and accurate introduction of the sample.

The operation of the sample introduction can be performed, as stated earlier, by only manually rotating the valve disc by way of the handle, being not only extremely simple but also very easy allowing any unskilled person to carry out the chromatographic separation. Besides, the amount of the sample can be selected at will, no matter how it may be minute such as 1 $\mu l$, or further minute less than 0.1 $\mu l$, because it can be definitely determined by the capacity of the sample flowing hole, which is calculated by the diameter and the depth of the hole (thickness of the valve disc). This invention can therefore be said very advantageous for the sample introduction to the micro-high-performance LC and other analysing apparatus.

BRIEF DESCRIPTION OF THE DRAWINGS

FIGS. 3 (a) and (b) are respectively descriptive views for explaining the operation of the device;

FIG. 4 is an elevational view of another embodiment of the valve disc of this invention; and FIG. 5 is a perspective view of the embodiment in FIG. 2 for explaining the mounted state thereof.

DETAILED DESCRIPTION OF THE PREFERRED EMBODIMENTS

Figure 1:
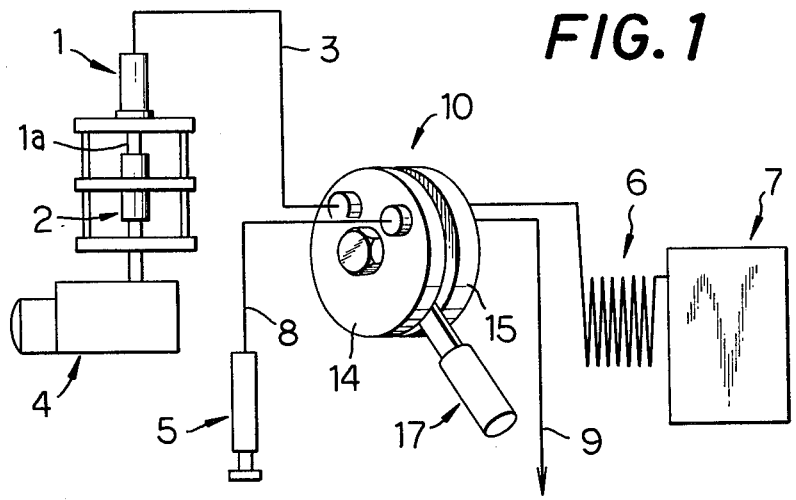
FIG. 1 is a schematic view of a micro-high-performance LC for explaining the entire structure thereof.
Figure 2:
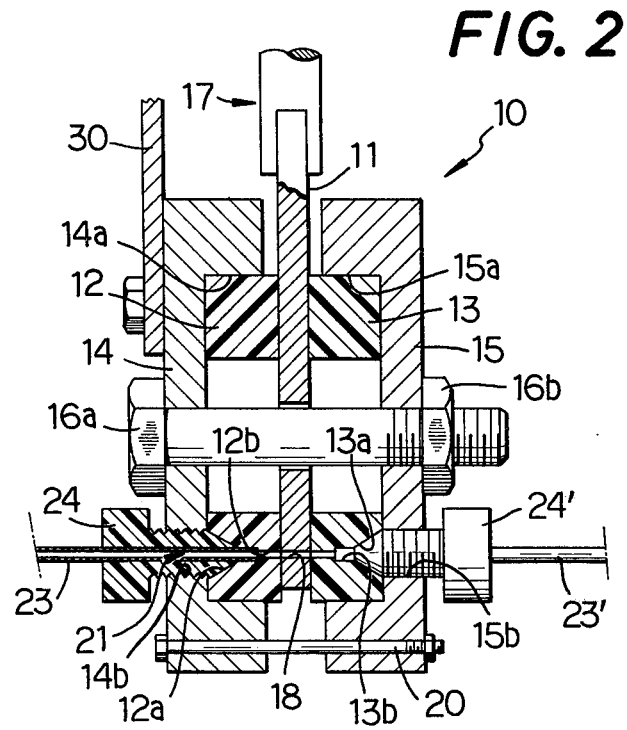
FIG. 2 is an axial sectional view of an embodiment of a micro amount sample introducing device of this invention.

With reference to FIGS. 1 and 2, which are a schematic view of an entire micro-high-performance LC system and an axial section of a sample introducing device of this invention, the structure of the device will be first described. Numeral 1 designates a pump syringe holding mobile phase solution (solvent) as a carrier fluid. A piston 1a disposed in the syringe 1 transports the mobile phase in the syringe 1, when it is axially moved by a pump driving screw 2, by way of a mobile phase transporting tube 3 to a separating column 6 (hereinafter simply called a column). The pump driving screw 2 is actuated by a driving mechanism, of which a detailed description is omitted because of its full disclosure being easy accessible in the above-mentioned U.S. Pat. No. 4,102,783.

The mobile phase transporting tube 3 is connected or communicated with a mobile phase flowing passage 21 in a sample introducing device 10 of this invention. The mobile phase supplied through the mobile phase transporting tube 3 is, after having been led to the mobile phase flowing passage 21, further led through an outlet thereof to the column 6 connected thereto. An injector (syringe) 5 containing a sample solution to be measured or analysed supplies the sample solution through a sample feeding tube 8 to the sample introducing device 10. The sample feeding tube 8 is connected to a sample flowing passage 22 (see FIG. 3) in the sample introducing device 10 for supplying the sample solution to the sample flowing passage 22 in the device, an outlet thereof being connected to a draining passage 9 for enabling the sample solution to be flowed away when it is necessary. On the downstream end or outlet end of the column 6 a well-known detector 7 is disposed, which is adapted to detect each ingredient of the sample developed through the analysis for describing a chromatogram.

The sample introducing device 10 disposed in such a state as shown in FIG. 1 includes a valve disc 11 of plate shape, a pair of annular bodies 12, 13 being rectangular in cross-section thereof, generally of dough-nut form, which are abuttingly pressed onto either side of the valve disc 11, a pair of outer plate members 14, 15 for embracing respectively one of the pair of annular bodies 12, 13 for pressing them from outer side, and a bolt 16a serving as an axle and a nut 16b for combining the valve disc 11, the pair of annular bodies 12, 13, and the pair of outer plate members 14, 15 as illustrated in FIG. 2. Further specifically stating, the valve disc 11 is provided with a handle for being gripped, which is a projection protruding sidewise as an extension from between the pair of outer plate members 14, 15. The valve disc 11 can be rotated about the axis, i.e., the bolt 16a; and the valve disc 11 made of stainless steel is so finished on its two surfaces by polishing as to be as smooth as a mirror, because it must be smoothly rotatable against the urging force of the pair of annular bodies 12, 13. The valve disc 11 is also provided with, on a same circumferential circle with its center at the rotation axis thereof, that is to say the combining bolt 16a, a mobile phase flowing hole 18 and a sample flowing hole 19 (see FIG. 3) having the same capacity as the sample amount to be introduced as the object of analysis, being arranged with a predetermined phase difference between the two and in a piercing manner through the valve disc 11.

The annular bodies 12, 13 are made of a hard synthetic resin into an annular form with a rectangular cross-section. They are pressed from either side so as to urge the surface of the valve disc 11 in a sandwiching manner to perform there complete sealing. Each abutting surface of the annular bodies 12, 13 onto the respective surface of the valve disc 11 is finished flat and smooth as a matter of course. And the annular bodies 12, 13 are fitted for being supported in an annular recess 14a, 15a formed respectively on the inner side of the pair of outer plate members 14, 15. The bolt 16a and the nut 16b cooperate to firmly combine the outer plate members 14, 15 together and urge the annular bodies 12, 13 at the same time onto either surface of the valve disc 11. The diameter of the central opening in each annular body 12, 13 is seen to be substantially greater than the diameter of the bolt 16a passing therethrough. It is necessary to fix the outer plate members 14, 15 not to be rotated accompanied by the rotation of the valve disc 11. In this embodiment one of the pair of outer plate members 14 is secured to one later described stationary member 30 and the two plate members 14, 15 are secured to each other with an anti-rotation pin 20 which fastens the both by piercing through them at the peripheral portion thereof. The sample introducing device 10 of this invention is, as illustrated in FIG. 5, secured by a retainer 30 which is mounted on a stand 40. A pair of flanges 30a extending from the retainer 30 are each provided with a stopper (screw) 31 threaded thereinto. The handle 17 of the valve disc 11 protruding outwardly or sidewardly is prevented from rotating beyond the stopper 31 by resting or abutting on the end surface of the stopper 31 at its own root portion.

Piercing through the annular body 12 and the outer plate member 14 as well as the corresponding annular body 13 and outer plate member 15 the mobile phase flowing passage 21 is formed at a position to be registered with the mobile phase flowing hole 18 in the valve disc 11. Just similarly to the above (see FIG. 3a) a sample flowing passage 22 is formed at a position to be registered with the sample flowing hole 19. The mobile phase flowing passage 21 and the sample flowing passage 22 formed through either set of the annular body and the outer plate member (for example 12 and 14) are of the same structure, so in FIG. 2 the mobile phase flowing passage only on one side is illustrated as a representative, the inlet side in this instance, others being omitted of illustration and description. Concretely speaking the structure of the mobile phase flowing passage 21 on the inlet side, it is constructed such that a connecting bolt 24 for connecting the supporting member 14 to the annular body 12, of fluoroethylene resin (for example polytetrafluoroethylene), which is tapered at the forward portion and contains therein a stainless steel pipe of predetermined diameter pierced therethrough in the axial direction, is fitted into a throughbore consisting of a tapered hole and a stepped hole forwardly positioned as a continuation thereof, both being formed in the annular body 12, so that the tapered portion of the connecting bolt 24 and the forward end portion of the stainless steel pipe 23 may be snugly or exactly settled there, by means of theading the connecting bolt 24 into a bore 14b formed in the outer plate member 14. Besides, the connecting bolt 24 is made of a synthetic resin not harder than one of which the annular body 12 (polytetrofluoroethylene in this embodiment) is made and the large diametered portion of the stepped hole 12b has a slightly smaller inner diameter than the outer diameter of the stainless steel pipe 23. Specifically speaking, in a case wherein the amount of the sample was 0.08 $\mu$l the inner diameter of the small diametered portion of the stepped hole 12b was determined at 0.3 mm$\phi$ and the inner diameter of the large diametered portion was 0.6 mm$\phi$, and on the other hand the outer diameter of the stainless steel pipe 23 was 0.65 mm$\phi$. By taking such a structure the dead volume of the mobile phase flowing passage 21 could be prevented from increasing to the best possible extent and the sample to be introduced was also effectively prevented from diffusing. To the stainless steel pipe 23 on the inlet side the mobile phase transporting tube 3 is connected and to the stainless steel pipe 23' on the outlet side the column 6 is connected. The structure of the mobile phase flowing passage 21 on the outlet side and that of the sample flowing passage on either the inlet and outlet sides are similar to the above described structure of the mobile phase flowing passage 21 on the inlet side, requiring no superfluous explanation.

Description will be proceeded to the way of introducing the sample into the separating (developing) column by means of utilizing the device of such a structure. Seeing the illustration in FIGS. 3 (a) and (b), the mobile phase from the pump syringe 1 can be on one hand flowed through, when the mobile phase flowing passage 21 on the inlet side and the outlet side is communicated through by the registered positioning of the mobile phase flowing hole 18 in the valve disc 11 with the mobile phase flowing passage 21, the same passage as far as the column 6; similarly on the other hand the sample solution supplied from the injector 5 through the sample feeding tube 8 can be flowed through the sample flowing passage 22, which is communicated through on the way by the sample flowing hole 19 in the valve disc 11, as far as the draining passage 9 connected to the outlet end of the sample flowing passage 22.

When the valve disc 11 is turned from one position shown in FIG. 3 (a) to the other position shown in FIG. 3 (b) as far as the handle 17 abuts the other stopper 31, while the sample flowing passage 22 and the sample flowing hole 19 are all filled with the sample solution, the sample flowing hole 19 is switched its position to the illustrated position. In other words, the sample flowing hole 19 can be moved to the position which has been occupied by the mobile phase flowing hole 18, since they are positioned on the same circumferential circle about the rotational axis of the valve disc 11 with a predetermined phase difference necessary thereto. By this switching-over of the valve disc 11 the mobile phase flowing passage 21 is communicated from the inlet side to the outlet side with the sample flowing hole 19 sandwiched therebetween in communicated state. And the sample flowing hole 19 is moved to the sandwiched position holding the sample in it, the volume thereof being equal to the capacity of the hole; the sample in the hole is kept as it is, until it is flowed to the column 6 by the flowing mobile phase, because the sample in the hole can be surely sealed by the annular bodies 12, 13 urged under pressure onto the either surface of the valve disc 11. The sample flowed by the mobile phase in a so to speak sandwiched state to the column 6 is subjected to the expected analysis or development. The rotation of the valve disc 11 in this way temporarily suspends the sample flowing passage 22 with the non-holed portion of the valve disc 11, and the sample in the passage is separated into two parts, the inlet side part and the outlet side part, which prevents the sample from being drained through the draining passage 9 irrespective of the sample feeding by the injector 5. When the analysis in the column 6 is, with the predetermined amount of the sample, finished the valve disc 11 is rotated to the original position shown in FIG. 3 (a) for being ready to the forthcoming analysis operation.

This invention has paved the way, as mentioned above in greater detail, to introduce the sample to the column in such a simple manner as to switch the sample flowing hole containing a predetermined amount of sample over to the predetermined position occupied by the mobile phase flowing hole, by means of rotating the valve disc by the predetermined angular distance. As the amount of the sample is definitely and unconditionally determined by the capacity (volume) of the sample flowing hole the personal variation according to the handling operation can be completely eliminated. As a result of this an accurate and good reproductive sample introduction has been advantageously achieved.

This invention should not be interpreted to be limited to the above embodiment. On the contrary many modifications and variations can be made within the spirit and scope of this invention.

For example of modifications, the valve disc 11 having a plurality of mobile phase flowing holes 18 and a plurality of sample flowing holes 19 is available; the capacity of this sample flowing hole can also be determined in any way according to the volume of the sample desired to be introduced, which may be selected based on the hole diameter and the thickness of the valve disc. In FIG. 4 another example of a valve disc with a double sample flowing holes 19' and 19'' is illustrated, with the mobile phase flowing hole 18 being sandwiched therebetween, on a same circumferential circle; as the two holes are different in the respective capacity thereof, chromatographic separation of different amount of the sample has advantageously become possible by the selection of the capacity.

The mobile phase flowing passage 21 and the sample flowing passage 22 which are formed piercing through the annular bodies 12, 13 and the outer plate members 14, 15 are respectively allowed to be formed in plural such as two or more. In case of those passages are formed respectively in plural, different kinds of mobile phases and samples may be advantageously selected or combined as desired. The pluralizing of the respective passages and that of the respective holes are not necessarily related, it should be rather determined by the type of sample introduction desired. In any way the pluralizing of the passage and/or the hole enables a variety of combinations between the passages and the holes according to the purpose of the employment of the device.

In the above embodiment the annular bodies and the outer plate members are utilized as the supporting or carrying means for the valve disc and this style is most preferable. However, it is also possible to form both in an integral body.

Furthermore this invention was originally made as a micro amount sample introducing device in an LC with an open-tubular micro-capillary column which was proposed by the inventors before in TOKU-KAI-SHO-54 (1979)-89691) and TOKU-KAI-SHO-54 (1979)-116296 (JAPAN), it is however employable in other types of chromatograph such as LC with a packed column and various other chromatographic separating apparatus, for example as a sample introducing device for a GC. It is necessited that a suitable gasifying device attached anywhere on the downstream, when it is utilized to a GC, for gasifying the solution state sample before being introduced. The sample to be introduced by this device may be a gas, not being limited to a liquid. The carrier fluid stated earlier also may be a gas, not being limited to a liquid.

Although this invention was described as a sample introducing device to a chromatograph, and particularly to an LC, it can also be advantageously applicable as a micro sample introducing device to various analysing apparatuses such as a mass spectrometer, emission spectro-analyser, atomic absorption spectrometer, etc.

This invention is unable in various ways like mentioned above and it should be understood to contain all of those in its category.

What is claimed is:

1. A device for introducing micro amount of sample into an analysing apparatus comprising a valve disc of plate form, rotatably disposed about an axle thereof perpendicular to the surface of the valve disc, and a pair of secured supporting members disposed on either side of, for urging from either side while supporting, said valve disc, and device characterized in that (1) said valve disc is provided with at least one carrier fluid flowing hole and at least one sample flowing hole having a capacity not exceeding 1 $\mu$l and having the identical capacity as a sample amount to be introduced, both holes being formed piercing through, and on a same circumferential circle with the center at the rotational axis of, said valve disc; (2) each of said supporting members is provided with at least one carrier fluid flowing passage and at least one sample flowing passage, both being formed piercing through each member at a position to be alignable with at least one of said carrier fluid flowing holes and at least one of said sample flowing holes; (3) said sample flowing hole communicated with said sample flowing passage can be moved to a position, owing to rotation of said valve disc, with a sample held therein at an amount identical to the interior capacity thereof, communicatable with the carrier fluid flowing passage; and (4) the sample held in said sample flowing hole is flowed together with a carrier fluid into said analysing apparatus wherein said pair of supporting members include respectively an annular body made of a synthetic resin for being urged onto the surface of said valve disc and an outer plate member having an annular recess for being fitted by said annular body, both being provided with said carrier fluid flowing passage and said sample flowing passage formed respectively piercing therethrough for being communicated with said carrier fluid flowing hole and said sample flowing hole respectively, the central opening in each said annular body having a diameter substantially greater than the diameter of said axle which passes therethrough.

2. A device in accordance with claim 1, wherein said at least one sample flowing hole all have a capacity not exceeding 0.1 $\mu$l.

3. A device in accordance with claim 1, wherein said valve disc is provided with at least two sample flowing holes which are different in capacity from each other, both having a capacity less than 1 $\mu$l.

4. A device in accordance with claim 1, wherein said analysing apparatus is a chromatographic separating apparatus, and a predetermined amount of the sample held in said sample flowing hole is led to a chromatographic separating column together with a mobile phase as the carrier fluid.

5. A device in accordance with claim 4, wherein said chromatographic separating apparatus is a micro-liquid chromatograph.

6. A device in accordance with claim 1, wherein said valve disc includes a circular plate portion, either surface thereof being finished flat and smooth like a mirror by polishing, and a handle portion protruding sidewise from said circular plate portion.

7. A device in accordance with claim 6, wherein said valve disc, said pair of annular bodies disposed on either side of said valve disc, and said outer plate members for supporting said pair of annular bodies and urging the same onto either surface of said valve disc are combined together with a bolt serving as said axle piercing through all of them, at least one of said outer plate members is secured to one stationary member of the device, and an anti-rotation pin is pierced through both outer plate members, thereby proventing said pair of annular bodies and said pair of outer plate members from being rotated with said valve disc when said valve disc is rotated with said handle about said bolt.

8. A device in accordance with claim 1, wherein at least one out of said carrier fluid flowing passage and said sample flowing passage extending through a said supporting member is formed by means of threading a connecting bolt, through which a stainless steel pipe is pierced in an axial direction thereof, with a tapered surface on a forward portion thereof, through said supporting member and into a through-bore consisting of a tapered hole and a stepped bore forwardly positioned as a continuation thereof, both being formed in said annular body, thereby fixing said supporting member to said annular body by fitting the forward tapered portion of said connecting bolt and a forward end portion of said stainless steel pipe snugly into said through-bore.

9. A device in accordance with claim 8, wherein said connecting bolt is made of a synthetic resin not harder than one of which said annular body is made, and a large diametered portion of said stepped-bore is smaller in its inner diameter than an outer diameter of said stainless steel pipe to be fitted thereinto.

10. A device in accordance with claim 1, wherein said annular bodies are formed of fluoro-resin and have surfaces which abut said valve disc which surfaces are finished flat and smooth.

11. A micro-high-performance chromatography device comprising a chromatography unit; a device for introducing micro amounts of sample into said chromatography unit; means for passing a carrier fluid through said device and into said chromatography unit; and means for passing a sample to said device whereby said device consistently separates a uniform micro amount of said sample and passes it to said carrier fluid whereby said carrier fluid delivers said micro amount of sample to said chromatography unit; and wherein said device for introducing micro amounts of sample into the chromatography unit comprises:

a valve disc in plate form rotatably disposed about a central axle thereof perpendicular to the surfaces of said valve disc; a pair of annular bodies made of synthetic resin and having central openings through which said axle passes, each annular body being disposed against an opposite surface of said valve disc, the diameters of the central openings of said annular bodies being substantially greater than the diameter of said axle; and a pair of secured supporting members disposed outside of said annular bodies urging said annular bodies against said valve disc;

said valve disc being provided with at least one carrier fluid flowing hole and at least one sample flowing hole having a capacity not exceeding 1 $\mu$l and having the identical capacity as a sample amount to be introduced, both said holes extending entirely through the thickness of said valve disc and being on the same circumferential circle with the center of the rotational axis of said valve disc, said holes being spaced around said circumferential circle a distance of less than 180°;

said supporting members and said annular bodies being provided with at least one carrier fluid flowing passage and at least one sample flowing passage, both of said passages extending entirely through said supporting members and said annular bodies at positions which are aligned with said carrier fluid flowing hole and said sample flowing hole extending through said valve disc;

means to rotate said valve disc between two fixed positions whereby said sample flowing hole communicating with said sample flowing passage can be moved to a position, owing to rotation of said valve disc, with a sample held therein at an amount identical to the interior capacity thereof, so as to communicate with the carrier fluid flowing passage, while said carrier fluid flowing hole is blocked off;

whereby the sample held in said sample flowing hole after said rotation of said valve disc is flowed together with a carrier fluid into said chromatography unit.

* * * * *